United States Patent
Choi et al.

(10) Patent No.: US 12,251,414 B2
(45) Date of Patent: Mar. 18, 2025

(54) PHARMACEUTICAL COMPOSITION FOR TREATING OR IMPROVING EDEMA AND BLOOD STASIS AFTER OPEN SURGERY

(71) Applicants: Young-jin Choi, Seoul (KR); Byung-hee Lee, Seoul (KR)

(72) Inventors: Young-jin Choi, Seoul (KR); Byung-hee Lee, Seoul (KR)

(*) Notice: Subject to any disclaimer, the term of this patent is extended or adjusted under 35 U.S.C. 154(b) by 0 days.

(21) Appl. No.: 18/633,642

(22) Filed: Apr. 12, 2024

(65) Prior Publication Data
US 2024/0382551 A1 Nov. 21, 2024

(30) Foreign Application Priority Data
May 19, 2023 (KR) .......... 10-2023-0065178

(51) Int. Cl.
| | | |
|---|---|---|
| *A61K 36/736* | (2006.01) | |
| *A61K 36/286* | (2006.01) | |
| *A61K 36/65* | (2006.01) | |
| *A61K 45/06* | (2006.01) | |
| *A61P 7/08* | (2006.01) | |

(52) U.S. Cl.
CPC .......... *A61K 36/736* (2013.01); *A61K 36/286* (2013.01); *A61K 36/65* (2013.01); *A61K 45/06* (2013.01); *A61P 7/08* (2018.01)

(58) Field of Classification Search
None
See application file for complete search history.

(56) References Cited

FOREIGN PATENT DOCUMENTS

| CN | 101711852 A | * 5/2010 |
|---|---|---|
| KR | 20150098436 | 8/2015 |
| KR | 10-2493427 B1 | 1/2023 |

OTHER PUBLICATIONS

Bai et al. (Effect of Massa Medicata Fermentata on the intestinal flora of rats with functional dyspepsia, Microbial Pathogenesis, vol. 174, Jan. 2023). (Year: 2023).*

Written Decision on Registration issued by the Korean Patent Office in corresponding KR Patent Application No. 10-2023-0065178 dated Nov. 16, 2023, with English translation.

Request for the Submission of an Opinion issued by the Korean Patent Office in corresponding KR Patent Application No. 10-2023-0065178 dated Jul. 20, 2023, with English translation.

Hyun-A Kim, et al., Anti-inflammatory and Anti-itching Effects of Herbal Medicine Complex Extracts(NI-01), Physical & Pathol Korean Med. 34(6): 341-347, pp. 1-7, 2020.

Hu Suk Lee, et al., "A Review of Pharmacological and Toxicological Studies on Safflower", J. Subtropical Agri & Biotech, Cheju National University, pp. 1-10, 2005.

* cited by examiner

*Primary Examiner* — Melissa S Mercier
(74) *Attorney, Agent, or Firm* — Carter, DeLuca & Farrell, LLP; George Likourezos, Esq.

(57) ABSTRACT

A pharmaceutical composition for treating or improving edema and blood stasis after open surgery according to an embodiment of the present disclosure includes an extract of a mixed herbal medicine including *Prunus persica* Batsch, *Carthamus tinctorius* Linni, and *Moutan radicis* Cortex as an active ingredient.

20 Claims, 10 Drawing Sheets

PHARMACEUTICAL COMPOSITION FOR TREATING OR IMPROVING EDEMA AND BLOOD STASIS AFTER OPEN SURGERY

CROSS-REFERENCE TO RELATED APPLICATION

This application claims priority to Korean Patent Application No. 10-2023-0065178 filed on May 19, 2023 and all the benefits accruing therefrom under 35 U.S.C. § 119, the contents of which are incorporated by reference in their entirety.

BACKGROUND

The present disclosure relates to a pharmaceutical composition for treating or improving edema and blood stasis after open surgery.

Edema refers to a condition which occurs when abnormally large amounts of body fluid and blood accumulate in damaged or inflammatory areas. Generally, when the damaged area swells, symptoms such as swelling of the area and thickening of the circumference appear. Edema may occur for a variety of reasons, including injury, surgery, sprains, allergic reactions, fever, and poor blood circulation.

Regarding therapeutic agents for treating edema, there is currently a very high demand worldwide. For example, the global diuretic market size reached USD 8.5 billion in 2020, which is expected to increase to USD 11.7 billion by 2025, and the demand is expected to continue to increase globally.

The therapeutic agents for treating edema are of various types and have various mechanisms of action, and come in various price ranges. For example, therapeutic agents such as diuretics and antihypertensives maintain a relatively low price range, while therapeutic agents such as anti-inflammatory drugs and antioxidants maintain a relatively high price range. In some countries, the prices of the therapeutic agents for treating edema are maintained at a relatively low level due to government subsidies, welfare policies, etc. However, in some countries, the therapeutic agents for treating edema are sold at high prices, and in order to resolve this problem, the government and pharmaceutical industry may need to work together to reduce prices, implement subsidies, etc.

Studies on oriental medicine for the treatment of edema are being conducted in various fields. Some studies have confirmed the effectiveness of treating edema using herbal medicines or herbal acupuncture. For example, studies to confirm the effectiveness of treating arm edema after stroke using herbal medicine acupuncture, studies to confirm the effectiveness of treating edema after abdominal surgery using complex herbal medicine treatment, etc. are being conducted. In addition, studies are being conducted to determine whether specific herbal medicines or herbal medicine prescriptions are effective in treating edema, and these studies show the possibility that oriental medicine may become an alternative method for treating edema.

Blood stasis, which is an oriental medical concept that refers to abnormally stagnant blood flow, is a term that refers to blood which has abnormalities in physiological functions in a state where blood flow is stagnant in the meridians and tissues, blood that escapes the blood vessels is discharged outside the body, or is not absorbed and accumulates under the skin.

Blood stasis may occur along with the above-mentioned edema due to damage to capillaries, etc. after open surgery.

If blood stasis is treated immediately as soon as it occurs, the degree of improvement will be good, but if blood stasis is left untreated, it may remain in the form of a 'bruise' or 'hard lump' and become difficult to treat later.

Related prior documents include Korean Patent No. 10-2493427.

Prior Art Document (Patent Document 1) KR Patent No. 10-2493427

SUMMARY

The present disclosure provides a pharmaceutical composition for effectively treating or improving edema after open surgery.

The present disclosure also provides a pharmaceutical composition for effectively treating or improving blood stasis after open surgery.

In addition to the above, embodiments according to the present disclosure may be used to achieve other purposes not specifically mentioned above.

In accordance with an exemplary embodiment of the present disclosure, a pharmaceutical composition for treating or improving edema and blood stasis after open surgery includes an extract of a mixed herbal medicine including well-ripen seeds of *Prunus persica* Batsch or *Prunus davidiana* Franchet, *Carthamus tinctorius* Linni, *Moutan radicis* Cortex, and *Massa medicata* Fermentata as an active ingredient.

The mixed herbal medicine may further include *Massa medicata* Fermentata.

The administration concentration of a pharmaceutical composition may be 0.013 g/mL to 0.053 g/mL.

In the mixed herbal medicine, the weight ratio between the well-ripen seeds of *Prunus persica* Batsch or *Prunus davidiana* Franchet, the *Carthamus tinctorius* Linni, the *Moutan radicis* Cortex, and the *Massa medicata* Fermentata may be 2:1:2:2.

In accordance with another exemplary embodiment of the present disclosure, a medicament for treating or improving edema and blood stasis after open surgery may include the pharmaceutical composition described above.

In accordance with still another exemplary embodiment of the present disclosure, a health functional food composition for treating or improving edema and blood stasis after open surgery may include the pharmaceutical composition described above.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
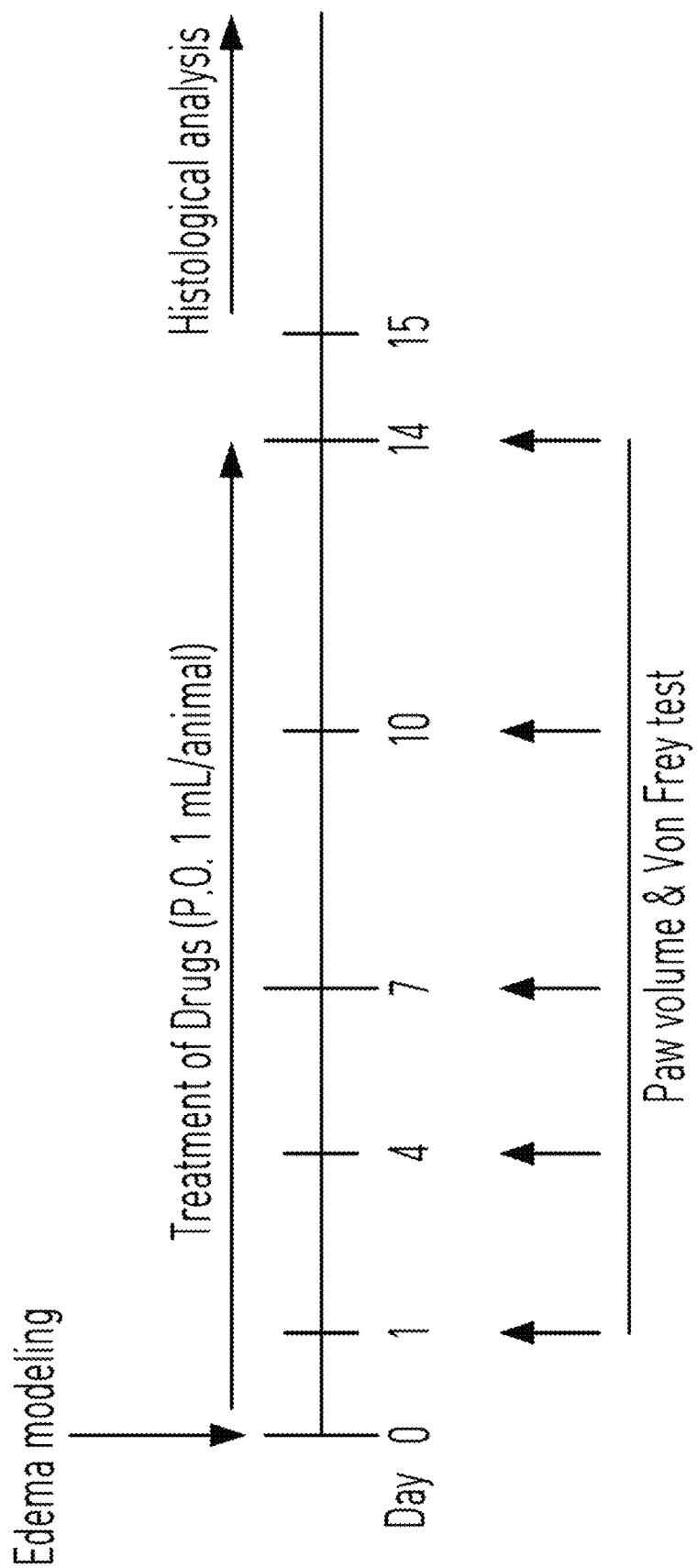
FIG. 1 is a diagram showing the experimental sequence and procedure in relation to the effect of pharmaceutical compositions according to embodiments.

Hereinafter, specific embodiments will be described in detail with reference to the accompanying drawings so that those skilled in the art can easily practice the same. The present disclosure may, however, be embodied in different forms and should not be construed as limited to the embodiments set forth herein. In order to clearly describe the present disclosure in the drawings, parts not related to the description are omitted, and the same reference numerals are used for identical or similar components throughout the specification. Additionally, in the case of well-known technologies in the art, detailed descriptions thereof are omitted.

In the drawing, the thickness is enlarged to clearly express various layers and areas. When a part of a layer, membrane, region, plate, etc. is described to be "on" another part, this includes not only a case where the part is being "directly above" the other part, but also a case where there is another part therebetween. Meanwhile, when a part is described to be "immediately on top" of another part, it means that there is no other part therebetween. In contrast, when a part of a layer, membrane, region, plate, etc. is described to be "beneath" another part, this includes not only a case where the part is being "directly below" another part, but also a case where there is another part therebetween. Meanwhile, when a part is described to be "immediately below" another part, it means that there is no other part therebetween.

Throughout the specification, when a part is described to "include" a certain component, this means that the part may further include another component rather than excluding another component, unless specifically stated to the contrary.

Throughout the specification, the term "composition" refers to a material in which two or more components are uniformly mixed, and is a concept that includes not only a finished product but also an intermediate material(s) for preparing the finished product.

As used herein, the term "edema" refers to a symptom that may occur as a result of an inflammatory response.

The present disclosure relates to a pharmaceutical composition for treating or improving edema and blood stasis that occur after open surgery, and it includes a novel composition exhibiting an excellent effect on treatment or improvement of edema, which is one of the symptoms that may occur after open surgery due to an inflammatory response, and blood stasis, that may occur after open surgery due to damage to capillaries, etc.

In addition, the pharmaceutical compositions according to the embodiments are harmless to the human body and have excellent safety because they are prepared based on natural medicinal materials, and their side effects may be minimized by including a plurality of non-toxic ingredients.

The pharmaceutical compositions according to the embodiments for treating or improving edema and blood stasis that occur after open surgery include an extract of a mixed herbal medicine including well-ripen seeds of *Prunus persica* Batsch or *Prunus davidiana* Franchet, *Carthamus tinctorius* Linni, and *Moutan radicis* Cortex as an active ingredient.

A pharmaceutical composition may reduce or remove edema that occurs after open surgery and may reduce or remove blood stasis, and thus, pain may be relieved.

In addition, the mixed herbal medicine may further include *Massa medicata* Fermentata.

The combination of well-ripen seeds of *Prunus persica* Batsch or *Prunus davidiana* Franchet, *Carthamus tinctorius* Linni, and *Moutan radicis* Cortex corresponds to a combination that is not known or disclosed in the pharmaceutical composition field for treating or improving edema and blood stasis. When the mixed herbal medicine includes well-ripen seeds of *Prunus persica* Batsch or *Prunus davidiana* Franchet, *Carthamus tinctorius* Linni, and *Moutan radicis* Cortex, it may significantly reduce or remove edema and blood stasis by a synergistic effect, compared to when the mixed herbal medicine includes only well-ripen seeds of *Prunus persica* Batsch or *Prunus davidiana* Franchet, and *Carthamus tinctorius* Linni.

In a case where the mixed herbal medicine includes all of well-ripen seeds of *Prunus persica* Batsch or *Prunus davidiana* Franchet, *Carthamus tinctorius* Linni, *Moutan radicis* Cortex, and *Massa medicata* Fermentata, a synergistic effect may occur, and thus, the effect of reducing or removing edema and blood stasis may be further improved. Specifically, in the case where the mixed herbal medicine includes all of well-ripen seeds of *Prunus persica* Batsch or *Prunus davidiana* Franchet, *Carthamus tinctorius* Linni, *Moutan radicis* Cortex, and *Massa medicata* Fermentata, the effect of reducing or removing edema and blood stasis may be more remarkable, compared to a case where the mixed herbal medicine includes each of well-ripen seeds of *Prunus persica* Batsch or *Prunus davidiana* Franchet, *Carthamus tinctorius* Linni, *Moutan radicis* Cortex, and *Massa medicata* Fermentata; a case where the mixed herbal medicine includes only well-ripen seeds of *Prunus persica* Batsch or *Prunus davidiana* Franchet and *Carthamus tinctorius* Linni; and a case where the mixed herbal medicine includes only well-ripen seeds of *Prunus persica* Batsch or *Prunus davidiana* Franchet, *Carthamus tinctorius* Linni, and *Moutan radicis* Cortex.

The combination including well-ripen seeds of *Prunus persica* Batsch or *Prunus davidiana* Franchet, *Carthamus tinctorius* Linni, *Moutan radicis* Cortex, and *Massa medicata* Fermentata corresponds to a novel combination which has never been known previously, and a pharmaceutical composition including this extract of such combination as an active ingredient also corresponds to a novel composition that has not been previously disclosed.

Based on the total weight of the mixed herbal medicine, well-ripen seeds of *Prunus persica* Batsch or *Prunus davidiana* Franchet may be contained in an amount of approximately 18 to 22 parts by weight, *Carthamus tinctorius* Linni may be contained in an amount of approximately 8 to 12 parts by weight, *Moutan radicis* Cortex may be contained in an amount of approximately 18 to 22 parts by weight, and *Massa medicata* Fermentata may be contained in an amount of approximately 18 to 22 parts by weight. More specifically, based on the total weight of the mixed herbal medicine, well-ripen seeds of *Prunus persica* Batsch or *Prunus davidiana* Franchet may be contained in an amount of approximately 20 parts by weight, *Carthamus tinctorius* Linni may be contained in an amount of approximately 10 parts by weight, *Moutan radicis* Cortex may be contained in an amount of approximately 20 parts by weight, and *Massa medicata* Fermentata approximately may be contained in an amount of 20 parts by weight. In this weight range, the effects on edema and blood stasis may appear more remarkably, and the synergistic effect due to the combination of each component may be maximized.

Based on the total weight of the mixed herbal medicine, the weight ratio between the well-ripen seeds of *Prunus persica* Batsch or *Prunus davidiana* Franchet, the *Carthamus tinctorius* Linni, the *Moutan radicis* Cortex, and the *Massa medicata* Fermentata may be 2:1:2:2. At this weight ratio, the effect of removing and reducing edema and blood stasis may be exhibited to be more excellent.

The concentration of the pharmaceutical compositions for treating or improving edema and blood stasis according to embodiments may be approximately 0.013 g/mL to approximately 0.053 g/mL. As used herein, the concentration may refer to the administration concentration of a pharmaceutical composition, and within this administration concentration range, the effect of treating or improving edema and treating or improving blood stasis may be more excellent.

More preferably, the concentration of the pharmaceutical compositions for treating or improving edema and blood stasis according to embodiments may be approximately 0.026 g/mL. At this administration concentration, the effect of treating or improving edema and the effect of treating or improving blood stasis may be exhibited at a more significant level.

A pharmaceutical composition includes an extract of a mixed herbal medicine as an active ingredient that has little toxicity or side effects, and thus, the pharmaceutical composition may be safely used even when it should be administered for a long time for preventive purposes.

Meanwhile, the pharmaceutical composition may include other pharmaceutically active ingredients other than the above-mentioned ingredients, or may be mixed with a pharmaceutical composition including other active ingredients to be used.

In order to prepare a pharmaceutical composition including an extract of a mixed herbal medicine, those skilled in the art may use any suitable method known in the art.

For example, a step of preparing a mixed herbal medicine and a step of hot water extraction are performed.

Hot water extraction may be performed, for example, at 80° C. to 140° C. for 2 to 3 hours, and within this range, extraction may be performed effectively without destruction or deterioration of the components of an extract. In particular, the weight of water may be approximately 5 to 10 times the weight of a mixed herbal medicine.

Then, a step of filtering the extract extracted by hot water extraction through a membrane filter is performed. In particular, the average pore size of the membrane filter may be approximately 0.5 μm to approximately 0.7 μm, and within this range, impurities may be effectively removed, and the extract may be effectively obtained.

Thereafter, the filtered extract may be freeze-dried and prepared in powder form, but the filtered extract is not limited thereto and may have various formulations.

The pharmaceutical composition according to an embodiment may be used as a medicament for treating or improving edema and blood stasis, depending on the desired method, the pharmaceutical composition may be administered to a patient by any means orally or parenterally (e.g., intravenously, subcutaneously, intraperitoneally, or topically applied), and although there is no particular limitation on the dosage form, it may be determined depending on the patient's age, sex, or severity of the disease.

In particular, solid preparations for oral administration may be in the form of powders, granules, tablets, capsules, soft capsules, pills, etc. Additionally, liquid preparations for oral administration may be in the form of suspensions, liquid preparations for internal use, emulsions, syrups, gels, aerosols, etc. Preparations for parenteral administration may be external preparations (e.g., powders, granules, tablets, capsules, sterilized aqueous solutions, solutions, non-aqueous solvents, suspensions, emulsions, syrups, suppositories, aerosols, etc.), respectively, according to conventional methods, or may be formulated and used in the form of a sterile injectable preparation. The preferred dose of the composition varies depending on the absorption, inactivation rate and excretion rate of the active ingredients in the body, the age, sex, and condition of the patient, and the severity of the disease to be treated, but may appropriately be selected by those skilled in the art.

The pharmaceutical composition according to an embodiment may further include commonly-used excipients, disintegrants, sweeteners, lubricants, flavoring agents, etc. For example, as excipients, substances such as lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, and polyvinyl pyrrolidone may be used. As disintegrants, for example, sodium starch glycolate, crospovidone, alginic acid, carboxymethyl cellulose calcium, carboxymethyl cellulose sodium, chitosan, guar gum, low-substituted hydroxypropyl cellulose, magnesium aluminum silicate, etc. may be used.

The pharmaceutical composition may further include a pharmaceutically acceptable additive. In particular, the pharmaceutically acceptable additive may include, for example, starch, gelatinized starch, microcrystalline cellulose, lactose, povidone, colloidal silicon dioxide, calcium hydrogen phosphate, lactose, mannitol, arabic gum, hydroxypropyl cellulose, sodium starch glycolate, carnauba wax, stearic acid, magnesium stearate, aluminum stearate, calcium stearate, white sugar, taffy, dextrose, sorbitol, talc, etc., but is not limited thereto. The pharmaceutically acceptable additive may be included in an amount of approximately 0.1 to 90 parts by weight based on the total pharmaceutical composition.

The pharmaceutical composition may be prepared by further including one or more pharmaceutically acceptable carriers for administration. In particular, the pharmaceutically acceptable carrier to be used may be saline, sterilized water, Ringer's solution, buffered saline, dextrose solution, maltodextrin solution, glycerol, ethanol, and a mixture of one or more of these ingredients.

A medicament for treating or improving edema and blood stasis after open surgery according to an embodiment of the present disclosure may include a pharmaceutical composition described above.

In addition, a health functional food composition for treating or improving edema and blood stasis after open surgery according to an embodiment of the present disclosure may include an extract of a mixed herbal medicine, which includes well-ripen seeds of *Prunus persica* Batsch or *Prunus davidiana* Franchet, *Carthamus tinctorius* Linni, and *Moutan radicis* Cortex, as an active ingredient. Additionally, the health functional food composition may include an extract of a mixed herbal medicine, which includes *Prunus persica* Batsch or *Prunus davidiana* Franchet, *Carthamus tinctorius* Linni, *Moutan radicis* Cortex, and *Massa medicata* Fermentata, as an active ingredient.

Hereinafter, the present disclosure will be described in more detail through examples and experimental examples, but the present disclosure is not limited thereto.

Comparative Example 1

A mixed herbal medicine including 18 g of well-ripen seeds of *Prunus persica* Batsch or *Prunus davidiana* Franchet and 9 g of *Carthamus tinctorius* Linmi was prepared.

Distilled water was added to the mixed herbal medicine to prepare 2.4 L of the composition, and then the composition was subjected to hot water extraction.

The hot water extract was filtered through a filter paper (Whatman No. 3, Maidstone, UK) and then freeze-dried to obtain the extract.

The extract was stored in a freezer maintained at approximately −20° C. until being used in experiments, and were sterilized using a sterilizing filter (pore size: 0.22 mm) immediately before the use in experiments.

Example 1

The mixed herbal medicine was prepared in the same manner as in Comparative Example 1, except that the mixed herbal medicine included 18 g of well-ripen seeds of *Prunus persica* Batsch or *Prunus davidiana* Franchet, 9 g of *Carthamus tinctorius* Linni, and 18 g of *Moutan radicis* Cortex.

Example 2

The mixed herbal medicine was prepared in the same manner as in Comparative Example 1, except that the mixed herbal medicine included 18 g of well-ripen seeds of *Prunus persica* Batsch or *Prunus davidiana* Franchet, 9 g of *Carthamus tinctorius* Linni, 18 g of *Moutan radicis* Cortex, and 18 g of *Massa medicata* Fermentata.

Example 3

The mixed herbal medicine was prepared in the same manner as in Comparative Example 1, except that the mixed herbal medicine included 9 g of well-ripen seeds of *Prunus persica* Batsch or *Prunus davidiana* Franchet, 4.5 g of *Carthamus tinctorius* Linni, 9 g of *Moutan radicis* Cortex, and 9 g of *Massa medicata* Fermentata.

Example 4

The mixed herbal medicine was prepared in the same manner as in Comparative Example 1, except that the mixed herbal medicine included 36 g of well-ripen seeds of *Prunus persica* Batsch or *Prunus davidiana* Franchet, 18 g of *Carthamus tinctorius* Linni, 36 g of *Moutan radicis* Cortex, and 36 g of *Massa medicata* Fermentata.

For experiments on the compositions according to Comparative Example 1 and Examples 1 to 4, animal models with edema were prepared, and divided into groups, and the edema removal effect was confirmed in ICR mice in which edema was induced in the soles of the feet after open surgery.

In order to determine the degree of edema, edema was induced in the right hind paw of each mouse, and herbal medicine was orally administered (1 mL/animal) once daily for 14 days. To confirm the changes in edema, the volume of the hind paw was measured on days 1, 7, and 14 after inducing edema. During the same period, mechanical allodynia was measured using a Von Frey filament. In order to confirm the effect of removing blood stasis after surgery, iron staining (Prussian blue staining) was performed.

The experimental progress schedule is shown in FIG. 1. The increase or decrease in body weight due to repeated administration of herbal medicine was not confirmed.

The herbal medicines used were standard medicinal drugs purchased from Entap Herb Co., Ltd. (Yangju-si, Gyeonggi-do) and Shinhung Pharmaceutical Co., Ltd. (Yeosu-si, Jeollanam-do).

The experimental animals used in this experiment were 6-week-old ICR male mice (20 g to 25 g) supplied by DBL (Eumseong-gun, Chungcheongbuk-do, Korea), acclimatized for one week, and then used to prepare animal models. During the experiment period, the animals were subjected to ad libitum feeding of a certain amount of solid feed and purified water, and the day/night cycle was 12 hours (daylight 08:00 to 20:00), and constant rearing conditions were maintained until the end of the experiment by maintaining an indoor temperature of 23±2° C. and humidity of 50±10%.

Animal Model with Hind Paw Edema

After inhalation anesthesia of the ICR mouse with isoflurane 2.0%, the skin on the heel of the right paw was incised, and then, plantar aponeurosis and flexor digitorum brevis were incised in three places approximately 5 mm in length using spring scissors. The incised area was instilled with kanamycin and the skin was sutured with biological glue.

Division of Groups

A total of 49 ICR mice were divided into a normal group (Nor, n=7), a control group in which edema-inducing ICR mice were treated with saline (Con, n=7), a group in which the composition according to Comparative Example 1 was administered to edema-inducing ICR mice (Comparative Example 1, n=7), a group in which the composition according to Example 1 was administered to edema-inducing ICR mice (Example 1, n=7), a group in which the composition according to Example 2 was administered to edema-inducing ICR mice (Example 2, n=7), a group in which the composition according to Example 1 was administered to edema-inducing ICR mice (Example 1, n=7), a group in which the composition according to Example 2 was administered to edema-inducing ICR mice (Example 2, n=7), a group in which the composition according to Example 3 was administered to edema-inducing ICR mice (Example 3, n=7), and a group in which the composition according to Example 4 was administered to edema-inducing ICR mice (Example 4, n=7). The medicinal drugs were each administered orally once daily in an amount of 1.0 mL/animal for a total of 14 times, and the normal group and the control group were administered with the same amount of saline.

All experimental results were shown after deriving the average value by performing at least three repeated experiments, and statistical significance was confirmed by two-way ANOVA (Bonferroni post hoc multiple comparison) and one-way ANOVA (Tukey's test) using the GraphPad Prism 8.0 analysis program (GraphPad Software, CA, USA).

Experimental Example 1—Measurement of Paw Volume

The paw volume of ICR mice was measured two or more times using a plethysmometer and the average value was calculated. The calculated average value was substituted into Equation 1 below to calculate the increase rate of edema. The paw volume of ICR mice was measured on days 1, 7, and 14.

$$\text{change rate of edema} (\Delta\text{Paw volume}) = \text{paw edema after inducing edema} - \text{paw edema before inducing edema} \quad [\text{Equation 1}]$$

The measurement results are shown in FIGS. 2A, 2B, 3A, and 3B.

Figure 2A:
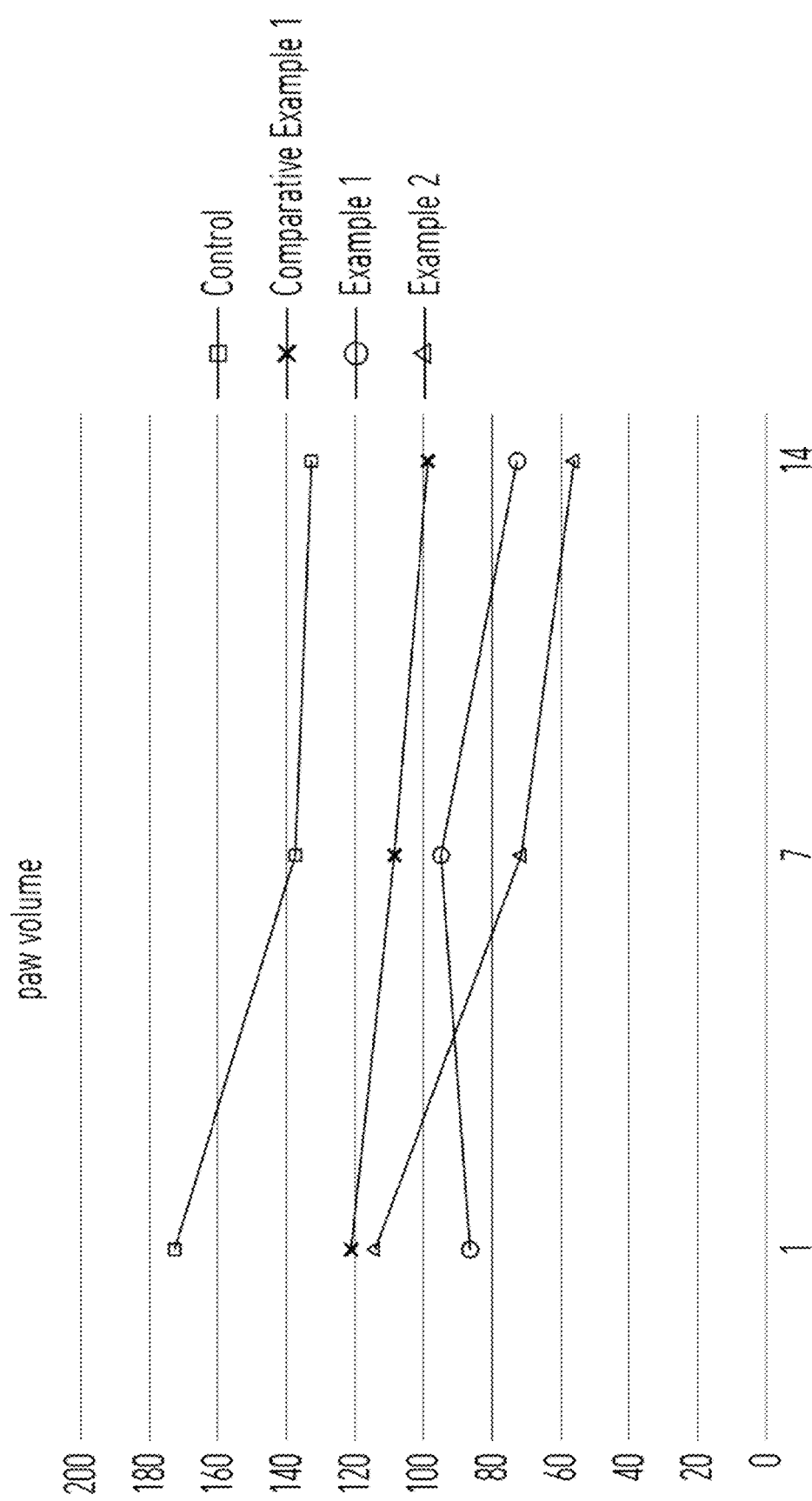
FIG. 2a is a graph showing the change in volume of the hind paws of mice according to administration of the pharmaceutical compositions prepared in Example 1, Example 2, and Comparative Example 1 for 14 days after inducing pain.
Figure 2B:
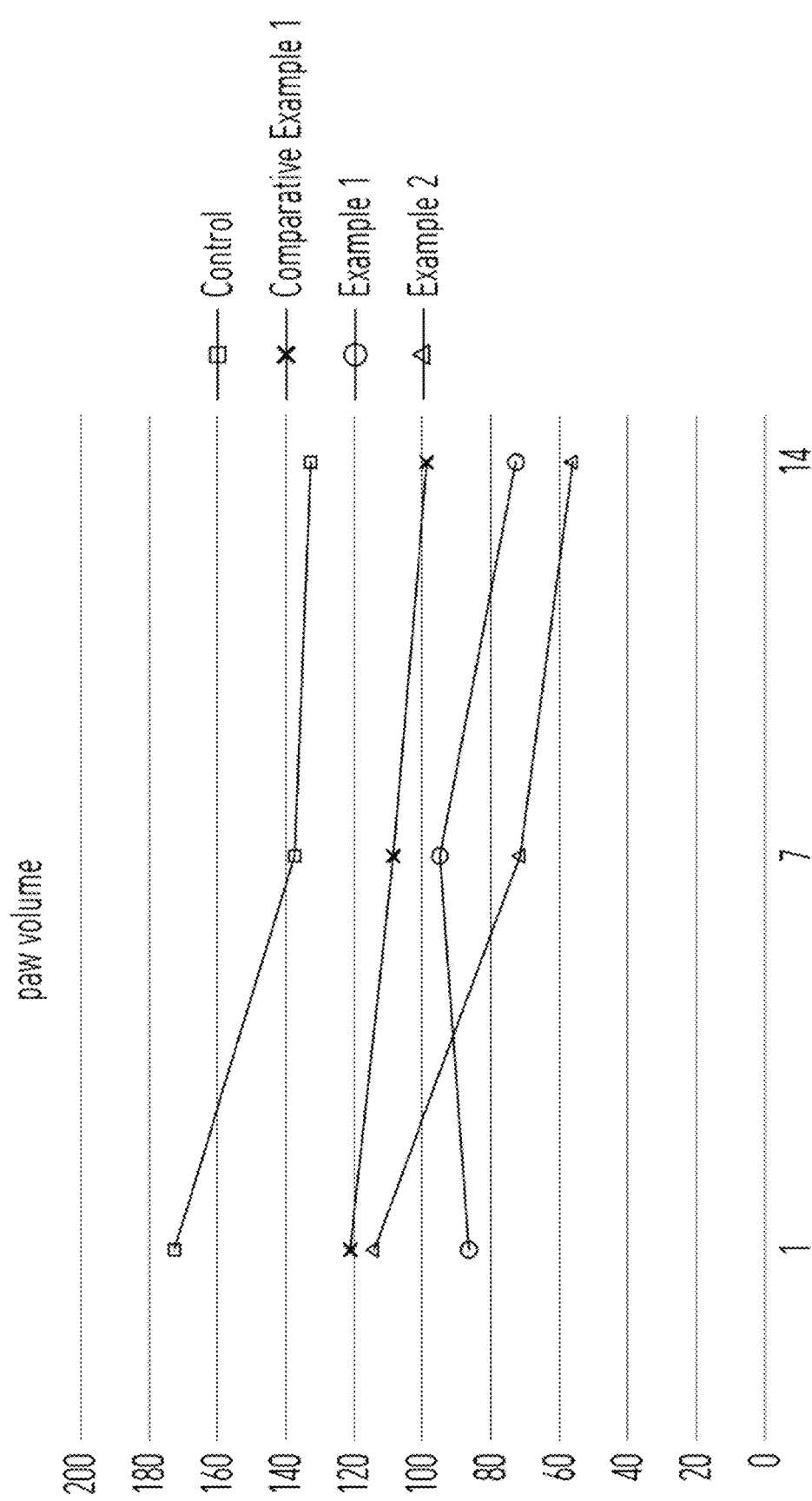
FIG. 2b is a graph showing the relative change in volume of the hind paws of mice based on that of day 1.

Referring to FIGS. 2A and 2B, the increase of edema after open surgery was statistically significant after day 1 and lasted for 14 days. When the composition according to Comparative Example 1 was administered to mice in which edema was induced, the edema was reduced compared to that of the control group, and on day 14 of administration, there was a statistically significant reduction compared to the control group. When the composition according to Example 1 was administered, the paw volume was significantly reduced compared to that of the control group from day 1, and continued until day 14. When the composition according to Example 2 was administered, the volume of the paw began to how a significant reduction from day 7, and the largest volume reduction was observed after day 14. When the relative volume reduction was checked based on day 1 of administration of the pharmaceutical composition (FIG. 2b), the administration of the composition according to Example 2 showed the largest rate of volume reduction.

Figure 3A:
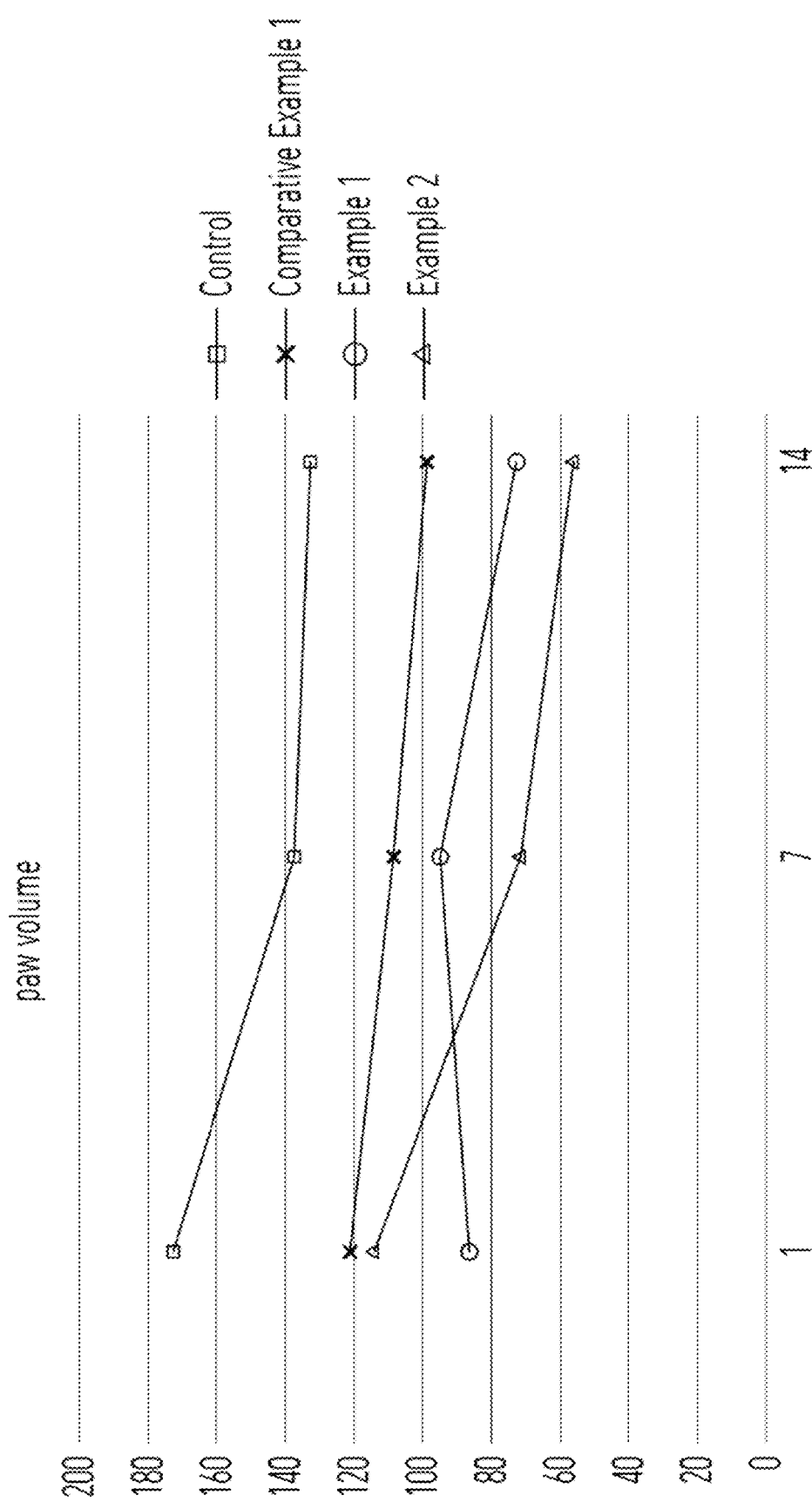
FIG. 3a is a graph showing the change in volume of the hind paws of mice according to administration of the pharmaceutical compositions prepared in Example 2, Example 3, and Example 4 for 14 days after inducing pain.
Figure 3B:
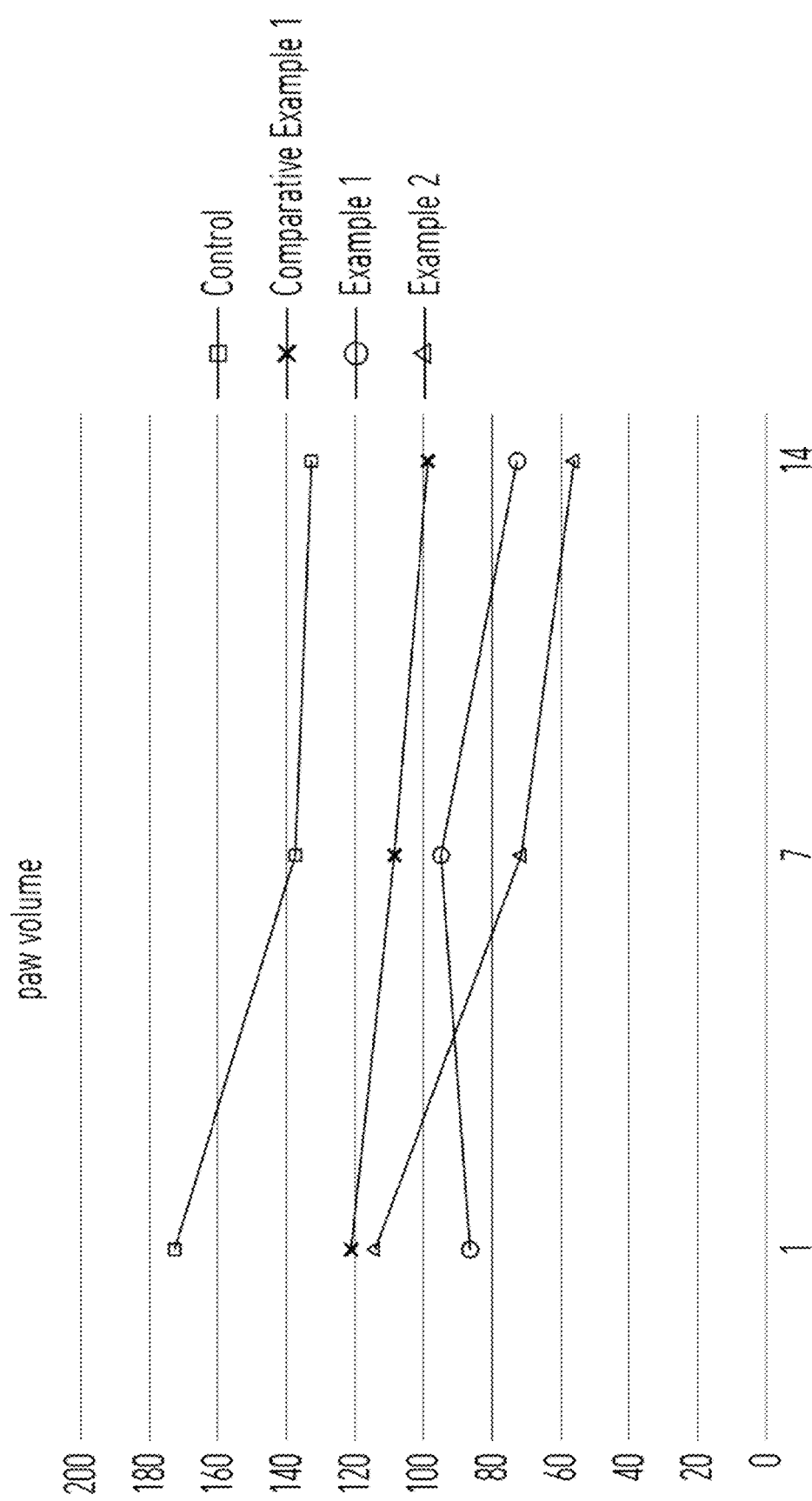
FIG. 3b is a graph showing the relative change in volume of the hind paws of mice based on that of day 1.

In order to use a mixed herbal medicine of the same composition and confirm the reduction in volume of mice paws according to the administration concentration, the compositions according to Examples 2 to 4 were administered to mice, and the results are shown in FIGS. 3A and 3B.

Referring to FIGS. 3A and 3B, all of the administration of the compositions according to Examples 2 to 4 significantly reduced the volume of the paws compared to that of the control group from day 1 to day 14. Additionally, when the composition according to Example 2 was administered, the highest edema reduction effect was observed.

Experimental Example 2—Measurement of Allodynia

The mechanical allodynia test was performed by applying physical stimulation to the sole of the paw using a Von Frey filament (Touch test 3.61 (0.4 g), North Coast Medical Inc., UK) and measuring the frequency of avoidance responses triggered in the soles. In order to measure the paw avoidance response, mice were placed in a transparent acrylic container (10 cm×10 cm×10 cm) with a grid placed on a 2 mm wire mesh and given time to adapt to the environment. After approximately 30 minutes, the mice compliance was checked and the soles of the feet were stimulated with quantified Von Frey filaments between the wire mesh grids. It was considered as a positive response if an avoidance response occurred during a total of 10 stimulations (a frequency of once per 10 seconds) on each hind paw to the extent that the Von Frey filaments were slightly bent. Allodynia was measured on days 1, 7, and 14.

The measurement results are shown in FIGS. 4A, 4B, 5A, and 5B.

Figure 4A:
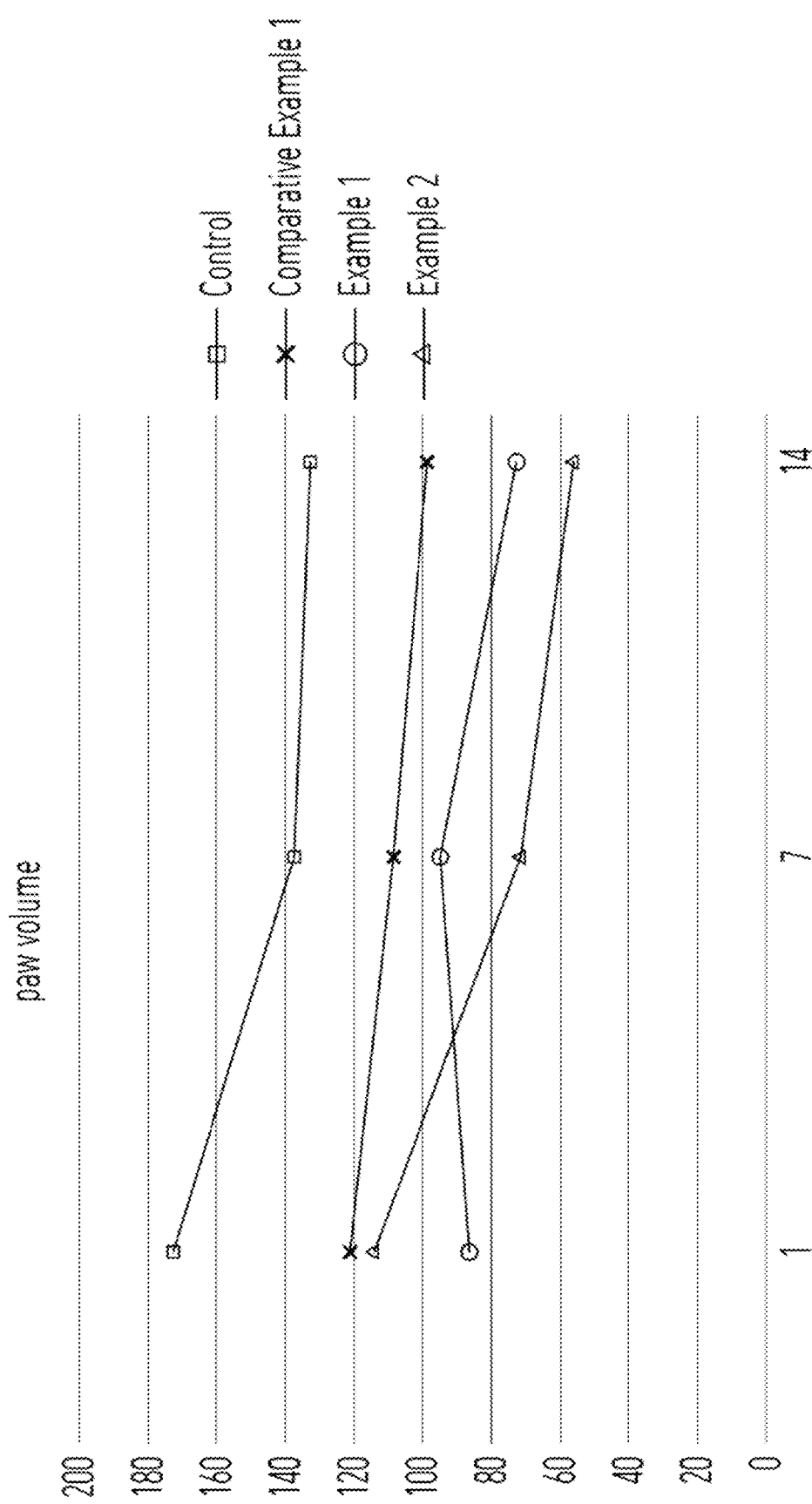
FIG. 4a is a graph showing the degree of mechanical allodynia of mice according to administration of the pharmaceutical compositions prepared in Example 1, Example 2, and Comparative Example 1 for 14 days after inducing pain.
Figure 4B:
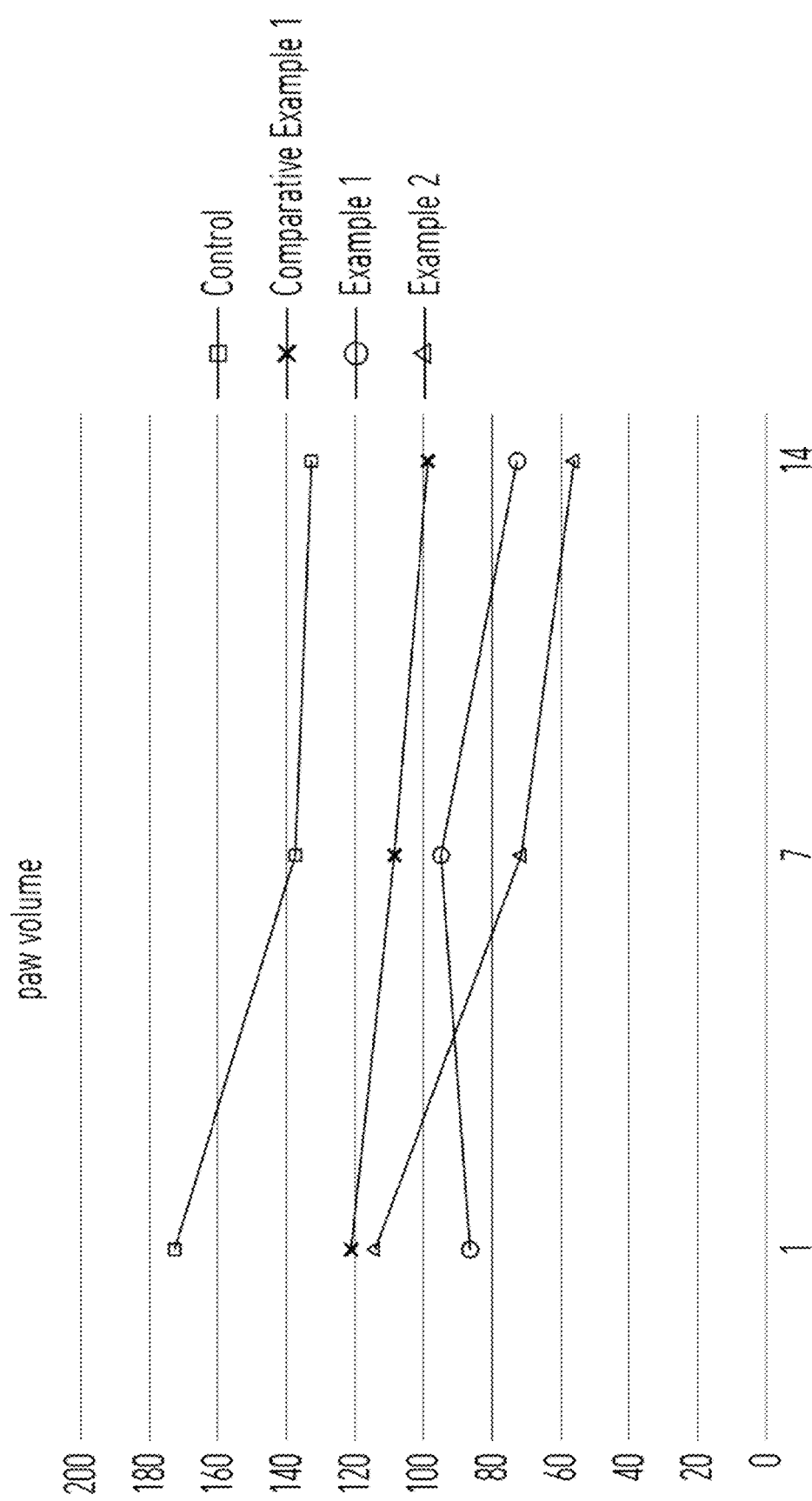
FIG. 4b is a graph showing the degree of mechanical allodynia of mice based on that of day 1.

Referring to FIGS. 4A and 4B, in the cases of the control, Comparative Example 1, and Example 1, pain was increased from day 1 to day 7, whereas in the cases of Comparative Example 1 and Example 1, the pain was decreased from day 7 to day 14. In the case where the composition according to Example 2 was administered, pain was continuously reduced. Additionally, it can be confirmed that when the compositions according to Examples 1 and 2 were administered, pain was significantly reduced.

Figure 5A:
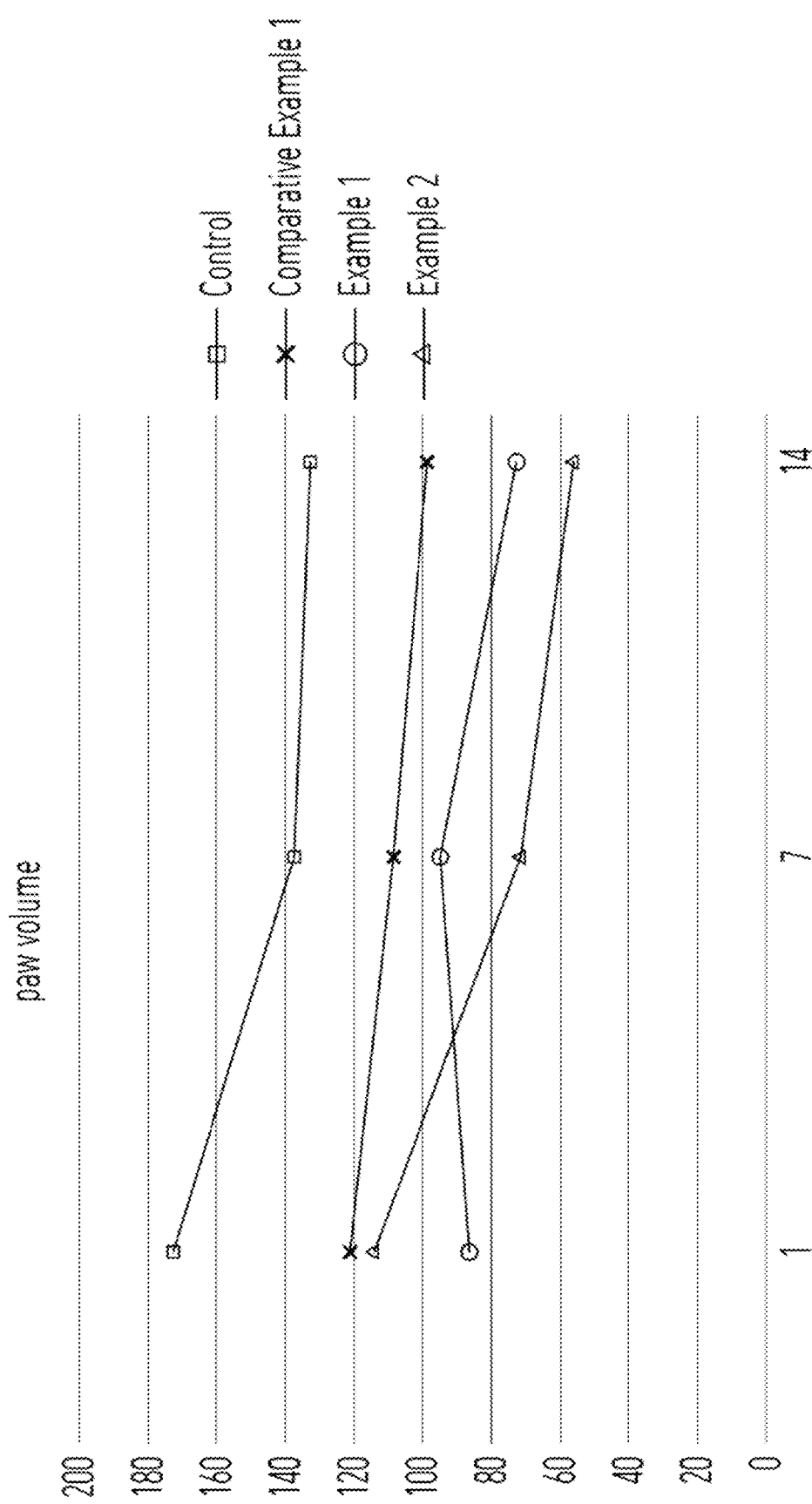
FIG. 5a is a graph showing the degree of mechanical allodynia of mice according to administration of the pharmaceutical compositions prepared in Example 2, Example 3, and Example 4 for 14 days after inducing pain.
Figure 5B:
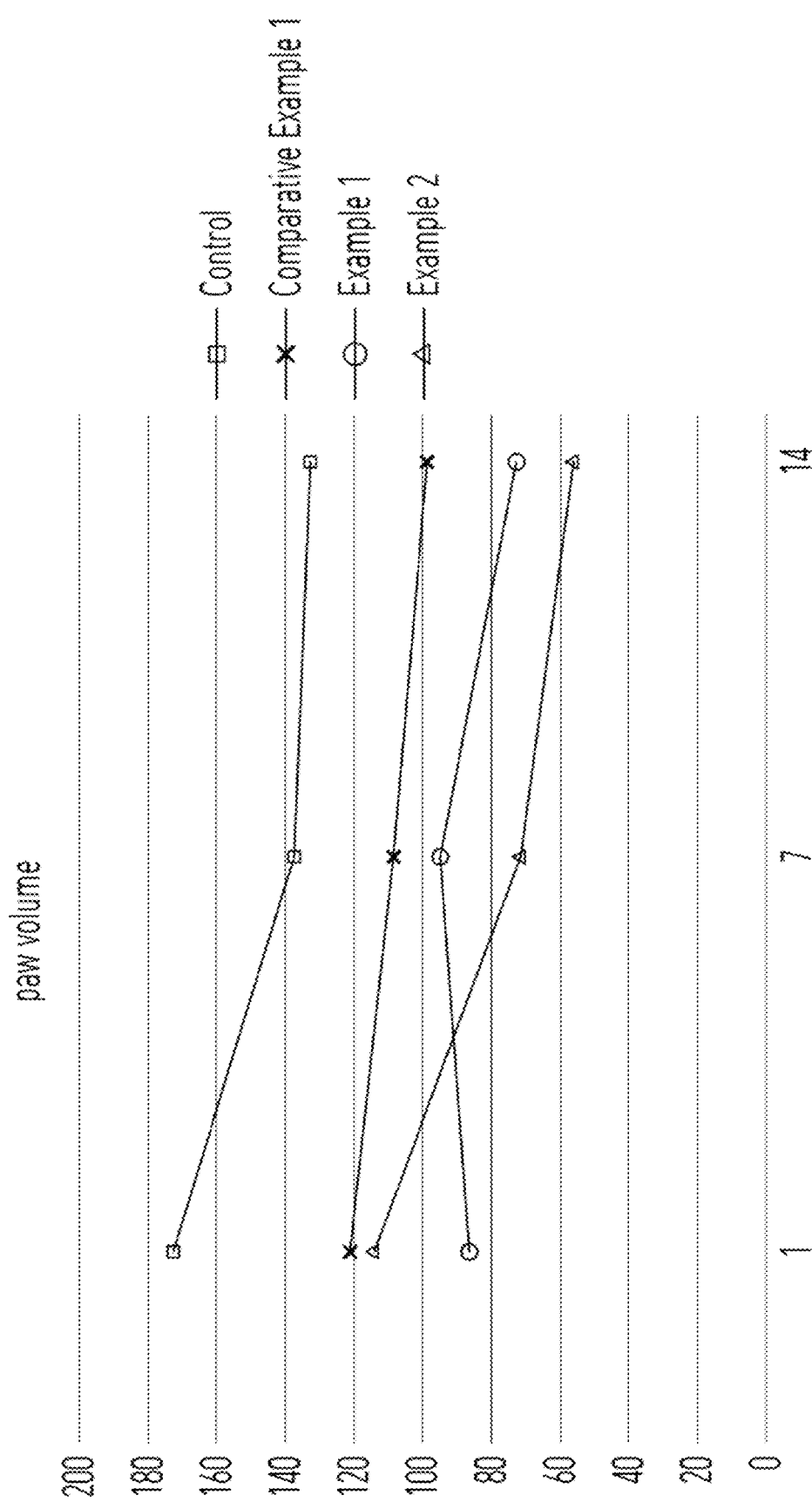
FIG. 5b is a graph showing the degree of mechanical allodynia of mice based on that of day 1.

A mixed herbal medicine of the same composition was used, and the compositions according to Examples 2 to 4 were administered to mice to confirm the reduction of mouse paw pain according to the administration concentration, and the results are shown in FIGS. 5A and 5B.

Referring to FIGS. 5A and 5B, in the case where the composition according to Example 2 was administered, the magnitude (degree) of pain was most significantly reduced.

Experimental Example 3—Iron Stain (Prussian Blue Iron Stain)

Subcutaneous bleeding due to surgery and Prussian blue iron stain may be directly or indirectly related. Subcutaneous bleeding is often caused by wounds, trauma, or decreased platelet count. In these cases, iron levels in the blood may rise excessively. Under these circumstances, Prussian blue iron stain may be used to detect iron status in the blood. Additionally, Prussian blue iron stain is also used to detect hemosiderin, and thus, it may also be used to detect hemosiderin deposition that may occur after subcutaneous bleeding. In this experimental example, the extent to which subcutaneous bleeding after surgery was reduced was confirmed through Prussians blue stain.

In order to confirm the presence of blood stasis in the tissue caused by the administration of the composition, Prussian blue stain was performed on sections of the soles of mice with induced edema. ICR mice were perfused through the heart with 50 mL of saline (PBS) followed by 80 mL of a 10% formalin solution prepared in phosphate buffer. The skin from the paw of each fixed ICR mouse was removed, post-fixed with the same fixative for 24 hours, placed in PBS containing 30% sucrose, and stored at 4° C. for one day. On the next day, the tissue was quickly frozen and then finely sectioned to a size of 5 µm to 10 µm. Equal amounts of a 20% aqueous solution of hydrochloric acid and a 10% aqueous solution of potassium ferrocyanide were mixed immediately before use and the mixture was used as a working solution. The sole skin tissue was incubated with the working solution for 20 minutes and then washed three times with distilled water. Counterstaining was performed with Nuclear Fast Red for 5 minutes and then the tissue was washed three times with triple distilled water. After completion of color development, the tissue was placed on a slide glass, dried at room temperature, dehydrated with 70%, 80%, 90%, 95%, and 100% ethanol, made transparent with xylene, and encapsulated with a Polymount. The degree of color development of each part of the brain tissue was observed under an optical microscope and the images were photographed.

Figure 6:
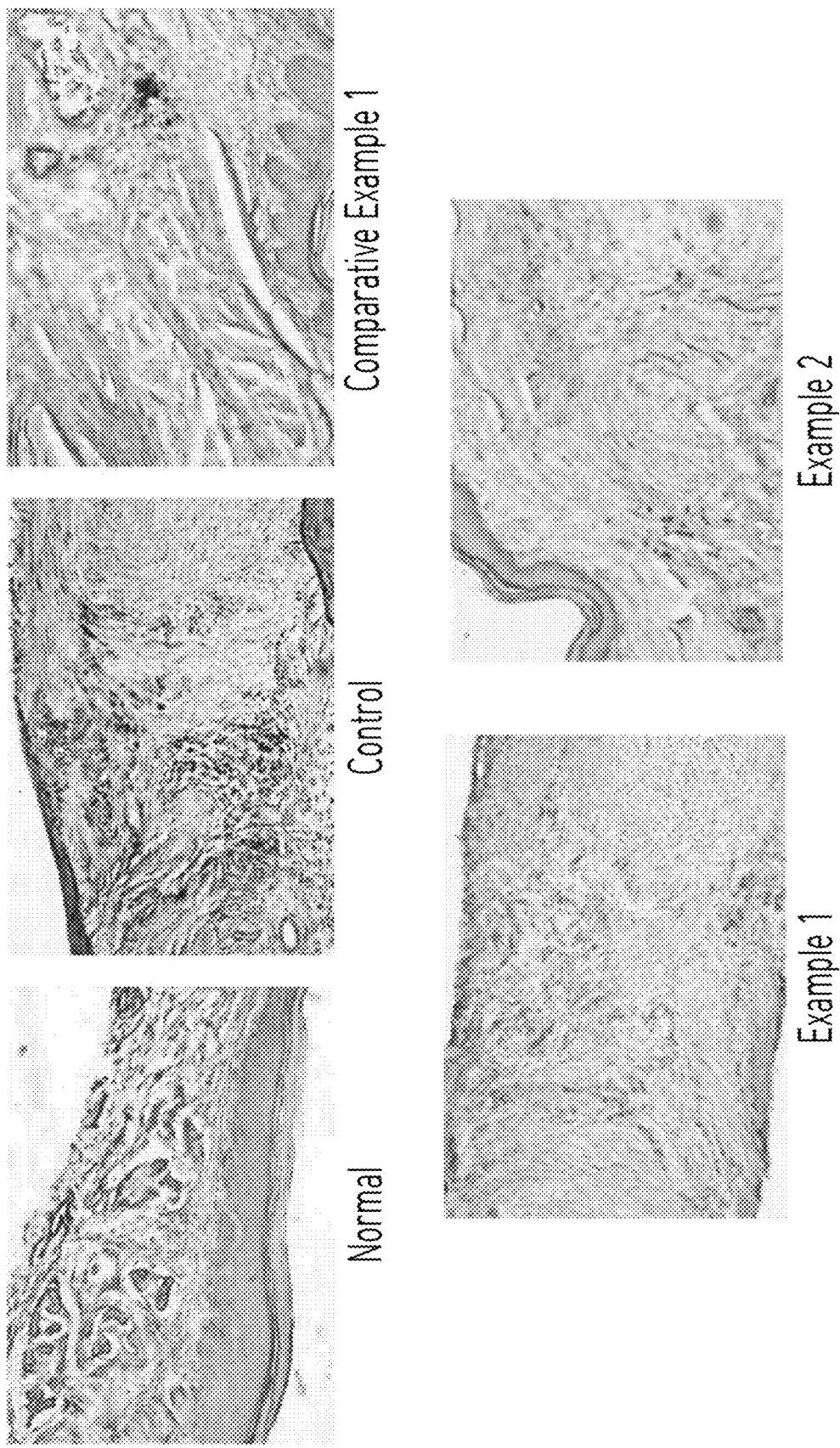
FIG. 6 is an image showing the results of the Iron Stain experiment.

The experimental results are shown in FIG. 6.

Referring to FIG. 6, the distribution of blood stasis in the tissue after open surgery was statistically significantly increased (see control). The administration of the composition according to Comparative Example 1 to edema-induced mice significantly reduced blood stasis, but the areas where blood stasis was intensively distributed remained. In contrast, the administration of the compositions according to Examples 1 and 2 relatively significantly removed blood stasis.

In an embodiment of the present disclosure, the pharmaceutical composition may effectively treat or improve edema and blood stasis after open surgery.

Although the preferred embodiments of the present disclosure have been described in detail above, the scope of rights of the present disclosure is not limited thereto, and various modifications and improvements, which were made by those skilled in the art using the basic concept of the present disclosure defined in the following claims, also fall within the scope of rights of the present disclosure.

What is claimed is:

1. A pharmaceutical composition for treating or improving edema after open surgery comprising:
    an extract of a mixed herbal medicine including *Prunus persica* Batsch, *Carthamus tinctorius* Linni, *Moutan radicis* Cortex, and *Massa medicata* Fermentata as an active ingredient; and
    a carrier, wherein the carrier is at least one of saline, sterilized water, Ringer's solution, buffered saline, dextrose solution, maltodextrin solution, glycerol, ethanol, or a mixture of one or more of these ingredients.

2. The pharmaceutical composition of claim 1, wherein the administration concentration of the pharmaceutical composition is 0.013 g/mL to 0.053 g/mL.

3. The pharmaceutical composition of claim 1, wherein in the mixed herbal medicine, the weight ratio between the *Prunus persica* Batsch, the *Carthamus tinctorius* Linni, the *Moutan radicis* Cortex, and the *Massa medicata* Fermentata is 2:1:2:2.

4. A medicament for treating or improving edema after open surgery, comprising the pharmaceutical composition of claim 1.

5. A health functional food composition for improving edema after open surgery comprising:
    an extract of a mixed herbal medicine including *Prunus persica* Batsch, *Carthamus tinctorius* Linni, *Moutan radicis* Cortex, and *Massa medicata* Fermentata as an active ingredient; and
    a carrier, wherein the carrier is at least one of saline, sterilized water, Ringer's solution, buffered saline, dextrose solution, maltodextrin solution, glycerol, ethanol, or a mixture of one or more of these ingredients.

6. The pharmaceutical composition of claim 1, wherein the pharmaceutical composition is administered as one of a powder, granule, tablet, capsule, soft capsule, or pill.

7. The pharmaceutical composition of claim 1, wherein the pharmaceutical composition is administered as one of a liquid suspension, emulsion, syrup, gel, or aerosol.

8. The pharmaceutical composition of claim 1, wherein the extract of the mixed herbal medicine is extracted via hot water extraction.

9. The pharmaceutical composition of claim 8, wherein the hot water extraction is performed at 80° C. to 140° C.

10. The pharmaceutical composition of claim 9, wherein the hot water extraction is performed for 2 to 3 hours.

11. The pharmaceutical composition of claim 8, wherein a weight of hot water is 5 to 10 times the weight of the mixed herbal medicine.

12. The pharmaceutical composition of claim 8, wherein the extract of the mixed herbal medicine extracted via hot water extraction is sieved through a membrane filter of about 0.5 μm to about 0.7 μm.

13. The pharmaceutical composition of claim 1, wherein the extract of the mixed herbal medicine is a powder.

14. The pharmaceutical composition of claim 1, wherein the extract of the mixed herbal medicine further includes *Prunus davidiana* Franchet.

15. The pharmaceutical composition of claim 1, wherein the pharmaceutical composition further comprises at least one of an excipient, disintegrant, sweetener, lubricant, or flavoring agent.

16. The pharmaceutical composition of claim 1, wherein the pharmaceutical composition further comprises an additive.

17. The pharmaceutical composition of claim 16, wherein the additive is at least one of starch, gelatinized starch, microcrystalline cellulose, lactose, povidone, colloidal silicon dioxide, calcium hydrogen phosphate, lactose, mannitol, arabic gum, hydroxypropyl cellulose, sodium starch glycolate, carnauba wax, stearic acid, magnesium stearate, aluminum stearate, calcium stearate, white sugar, taffy, dextrose, sorbitol, or talc.

18. The pharmaceutical composition of claim 17, wherein the additive is included in an amount of 0.1 to 90 parts by weight based on the pharmaceutical composition.

19. The health functional food composition of claim 5, wherein the extract of the mixed herbal medicine further includes *Prunus davidiana* Franchet.

20. The health functional food composition of claim 5, wherein the health functional food composition further comprises at least one of an excipient, disintegrant, sweetener, lubricant, or flavoring agent.

* * * * *